United States Patent [19]
Porowski et al.

[11] Patent Number: 5,354,307
[45] Date of Patent: Oct. 11, 1994

[54] SURGICAL MEANS FOR REMOVING A PORTION OF A BODY

[76] Inventors: Jan S. Porowski, 534 Glen Arden Dr., Pittsburgh, Pa. 15236; Edward J. Hampton, 4100 Verner Dr., Murrysville, Pa. 15668

[21] Appl. No.: 136,096

[22] Filed: Oct. 14, 1993

Related U.S. Application Data

[63] Continuation of Ser. No. 863,742, Apr. 6, 1992, abandoned.

[51] Int. Cl.⁵ .............................. A61B 17/32
[52] U.S. Cl. .................... 606/171; 606/170; 606/174; 606/172
[58] Field of Search ............... 30/165, 237, 241, 278, 30/279.2, 280, 299, 301, 306; 604/22, 313, 115; 128/751, 752, 757, 758; 606/123, 131, 133, 167, 170, 171, 172, 174, 110, 165

[56] References Cited

U.S. PATENT DOCUMENTS

| | | | |
|---|---|---|---|
| 593,524 | 11/1897 | Helbig | 30/280 |
| 2,945,496 | 7/1960 | Fosdal | 604/115 |
| 3,160,493 | 12/1964 | Kuppers | 30/241 |
| 4,299,219 | 11/1981 | Norris, Jr. | 604/115 |
| 4,662,376 | 5/1987 | Belanger | 604/115 |
| 5,106,364 | 4/1992 | Hayafuji et al. | 606/171 |

*Primary Examiner*—C. Fred Rosenbaum
*Assistant Examiner*—N. Kent Gring
*Attorney, Agent, or Firm*—Roylance, Abrams, Berdo & Goodman

[57] ABSTRACT

Surgical means for removing a portion of a body comprising means for applying a vacuum upon the portion of the body to be removed sufficient to move such portion away from the remainder of the body immediately adjacent to such portion and means for cutting such portion of the body that has been moved to sever it from the remainder of the body. The invention is also directed to a process for removing a portion of the body wherein a vacuum is applied to such portion and thereafter is severed from the remainder of the body.

12 Claims, 4 Drawing Sheets

SURGICAL MEANS FOR REMOVING A PORTION OF A BODY

This is a continuation of application Ser. No. 07/863,742 filed on Apr. 6, 1992 now abandoned.

BACKGROUND OF THE INVENTION

1. Field of the Invention

This invention relates to (1) surgical means for removing a portion of a body which comprises means for applying a vacuum, or negative pressure, upon said portion of said body sufficient to move the same away from the remainder of said body adjacent thereto and means for cutting said portion of said body so moved to sever said portion of said body from the remainder of said body and (2) a process for applying a vacuum upon a portion of a body sufficient to move the same away from the remainder of said body adjacent thereto and then cutting said portion of said body so moved to sever said portion of said body from the remainder of said body.

2. Description of the Art

Portions of the body, within said body or on the surface thereof, are often removed therefrom for medical reasons or, in some cases, for aesthetic purposes. Examples of such portions that are removed are moles or nevus, corns, cysts and cancerous growths, as well as organs, such as gallbladders. It is common, for example when said materials to be removed are on the surface of the body, to carry out the process surgically by first treating the same with an anesthetic to reduce any pain or discomfort that may arise from such excision and then removing the same by cutting to a depth to remove all of the undesired material plus any associated components thereof, such as roots, etc. Such removal is difficult, time consuming, can require unnecessarily long recovery periods and can result in much patient discomfort. When such removal must be made in the interior of the body and especially when the removal of an internal organ, such as a gallbladder is involved, rather large openings must be made into the body interior, resulting in even greater operating difficulties and patient discomfort. Moreover, the removal must be complete, because leaving behind even very small portions of material to be removed can result in regrowth thereof.

In British Patent No. 965,111, Summersgill discloses a device for removing corns from a body comprising a manually-operated, suction-producing device having annular cutting means at its forward part for cutting the epidermis surrounding the corn, sot hat when suction is applied to the corn, by the suction-producing device, the corn will be raised against the cutting edge of the cutter, thus cutting the epidermis, and pulling out the portion of the epidermis, with the flesh attached thereto, within the area so cut, from the rest of the body.

Kirk in British Patent No. 351,314 discloses the use of a vacuum to extract growths and foreign matters, such as corns or bunions, from the body after a chiropodist has prepared the same to be extracted. How the chiropodist prepares the corn or bunion for extraction is not disclosed.

Niebel discloses in U.S. Pat. No. 3,807,405 a device for removing moles which comprises a spring-loaded plunger carrying a razor-like blade at the end thereof provided with means so that when the plunger is pressed downwardly the blade rotates about 180° to penetrate the skin, thereby making an elliptical-shaped cut therethrough, thus excising the mole from the body.

Baye in German Patent DE removes unwanted particles on the skin, such as acne, by pressing on the acne and then removing the same by a combination of adhesion and suction.

Using the surgical device disclosed and claimed herein, we easily remove the undesired portion of the body from the remainder thereof adjacent thereto, by applying a vacuum on said portion of body sufficient to move the same away from the remainder of said body adjacent thereto and then cutting said portion of said body so moved to sever said portion of said body from the remainder of said body.

BRIEF DESCRIPTION OF THE INVENTION

Our invention relates to a surgical device for removing a portion of a body which comprises means for applying a vacuum upon said portion of said body sufficient to move said portion of said body away from the remainder of said body immediately adjacent thereto and means for cutting said portion of said body so moved to sever said portion of said body so moved from the remainder of said body. Our invention also relates to a process for surgically removing a portion of a body which comprises applying a vacuum upon said portion of said body sufficient to move said portion of said body away from the remainder of said body immediately adjacent thereto and thereafter cutting said portion of said body so moved to sever said portion of said body so moved from the remainder of said body.

Figure 1:
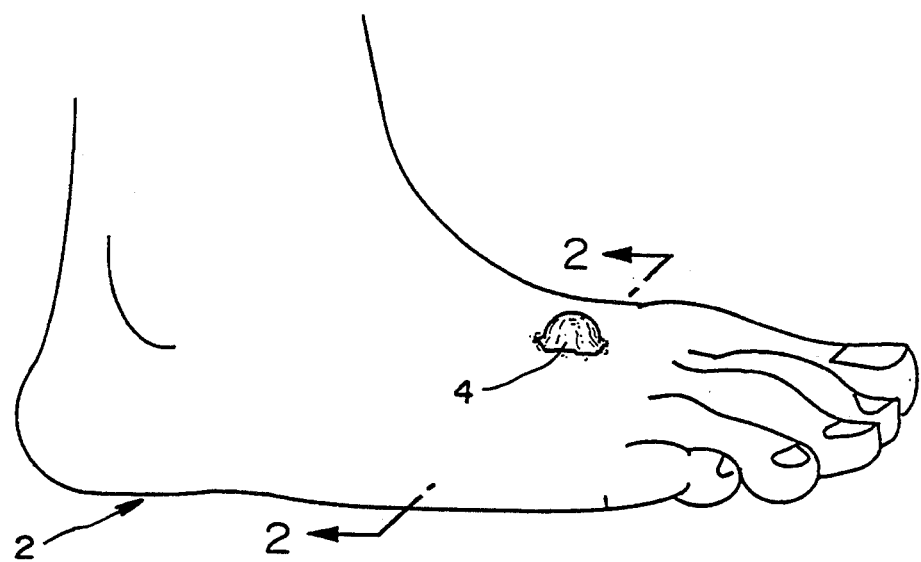
FIG. 1 is a perspective view of a foot having on the surface thereof a mole to be excised therefrom.
Figure 2:
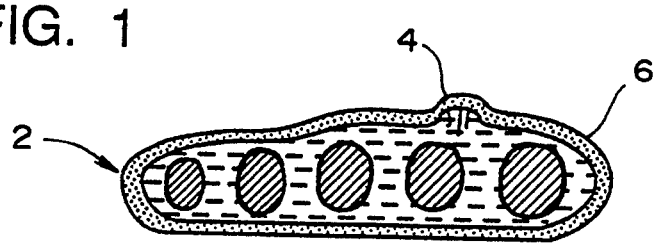
FIG. 2 is a cross-section of the foot of FIG. 1 taken along the line 2—2 therein.

Referring to FIG. 1, there is shown a foot 2 carrying on a portion thereof a mole 4 which is desired to be removed. In FIG. 2, which is a cross-section taken along the line 2-2 in FIG. 1, it can be seen that mole 4 extends upwardly from the epidermis 6 immediately adjacent thereto and substantially removed from the bones in the foot 2.

Figure 3:
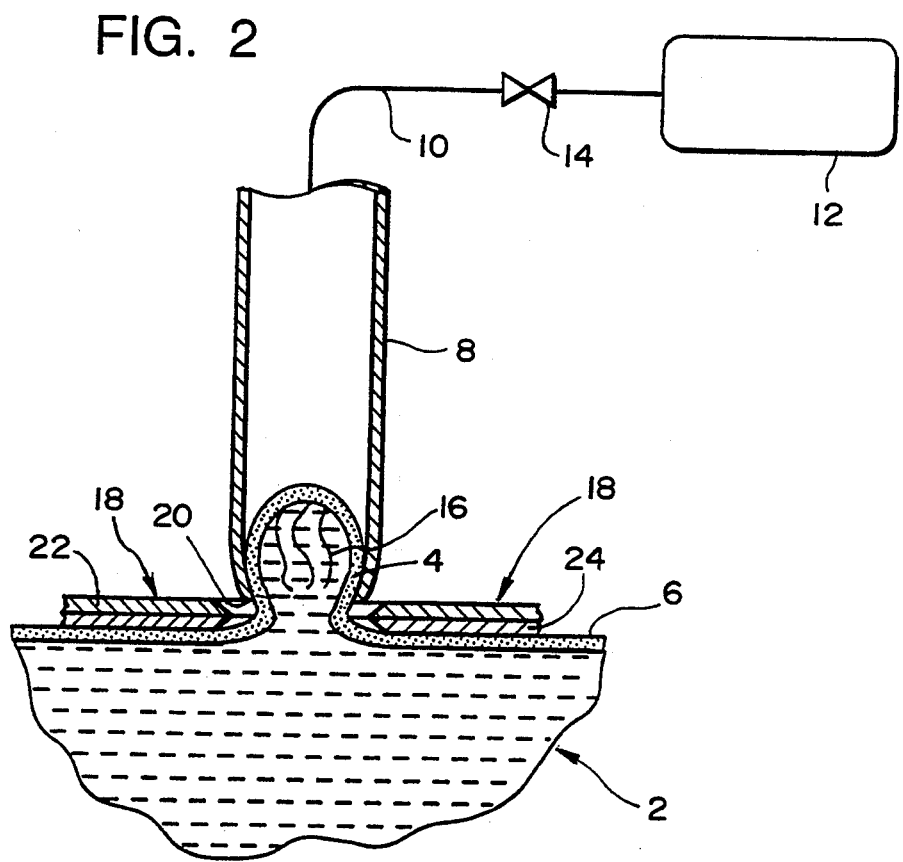
FIG. 3 is also a cross-section of the foot of FIG. 1, but wherein a vacuum has been applied to the mole to lift the same above the level of the remainder of the foot adjacent thereto.

FIG. 3 discloses an embodiment used herein for removing a portion of the body therefrom, in this case the mole 4. As seen, the mole 4 is moved away from the surface of foot 2 by lifting the same upwardly above the level of the adjacent epidermis into the lower portion of elongated tube 8. In FIG. 3 this is done by applying a vacuum upon said mole 4 through a line 10 extending from elongated tube 8 to vacuum source 12. Line 10 is provided with a valve 14 to control the amount of vacuum desired in elongated tube 8. The vacuum source need not be described specifically, for any vacuum source capable of applying the desired vacuum to elongated tube 8 can be used. The amount of vacuum needed is that amount sufficient to move all of the portion of the body desired to be removed, including portions associated therewith, such as roots 16, away from the remainder of said body immediately adjacent thereto so that when cutting means 18 are actuated all of the portion of the body desired to be removed are severed therefrom. Thus, the amount of vacuum needed will be in the range of about 200 to about 760 mm Hg. In the embodiment of FIG. 3, the free end portion 20 of the elongated tube 8 is curved inwardly so that when the portion of the body is dispersed therein a stronger vacuum seal is maintained therein. The lower portion of elongated tube 8 can be either circular or elliptical in cross-section as long as the cross-sectional area thereof is sufficient to adequately surround the portion of the body to be excised. Elongated tube 8 can be made of any material, such as metal, glass or plastic, but preferably glass.

Figure 4:
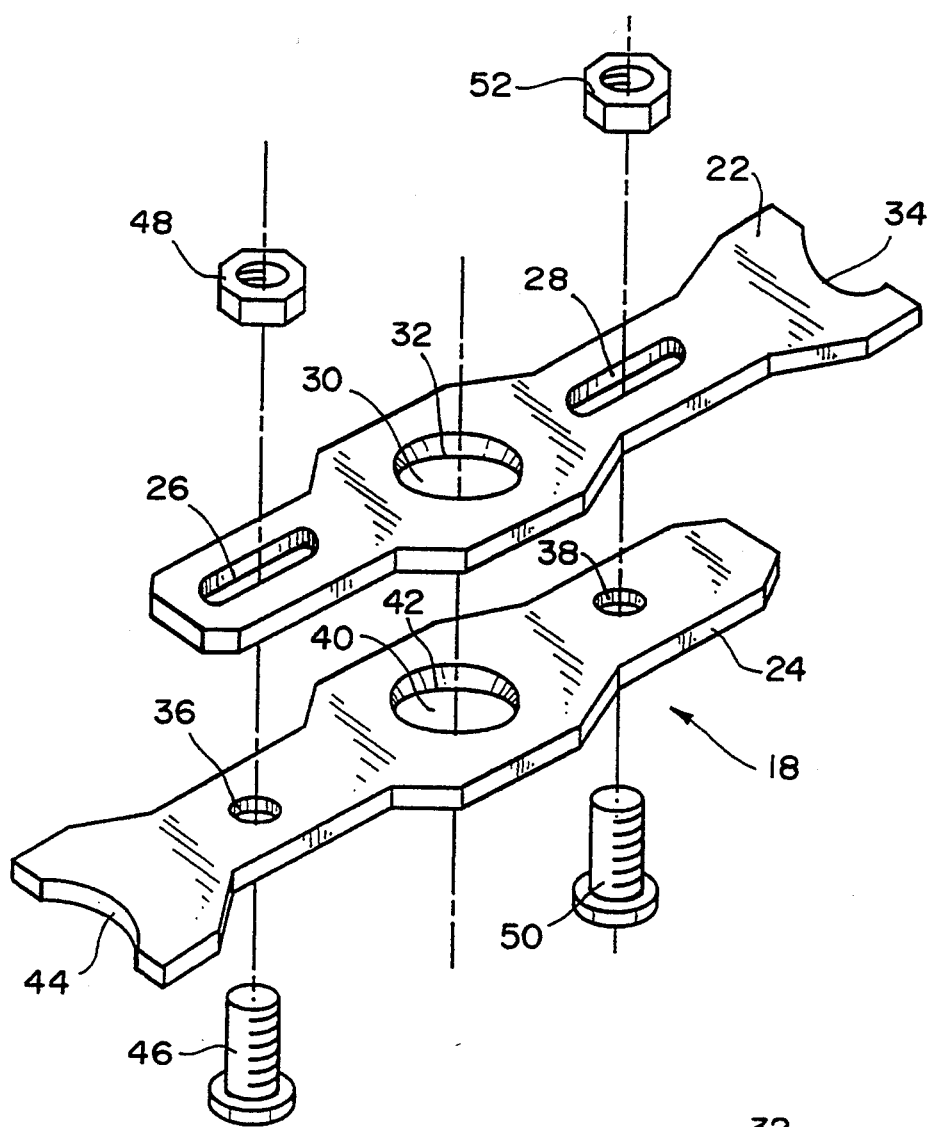
FIG. 4 is an exploded perspective view of a cutting device that can be used herein.

The specific cutting means 18 used herein are not critical as long as they are adequate to sever the portion of the body to be removed from the remainder of the body when said portion is lifted or moved away from the remainder of the body adjacent thereto. One such cutting means that can be used herein is illustrated in FIG. 4 comprising two elongated, essentially flat metal bodies 22 and 24. Elongated metal body 22 is provided with elongated slots 26 and 28, an opening 30 having a cutting edge 32 and a notch portion 34. Elongated metal body 24 is provided with openings 36 and 38, an opening 40 having a cutting edge 42 and a notch portion 44. The cutting device 18 is easily assembled by passing a bolt 46 upwardly through opening 36 in elongated metal body 24 and then through elongated slot 26 in elongated metal body 22, after which nut 48 is threaded onto bolt 46. Similarly, bolt 50 is passed upwardly through opening 38 in elongated metal body 24 and then through elongated slot 28 in elongated metal body 22, after which nut 52 is threaded onto bolt 50.

Figure 5:
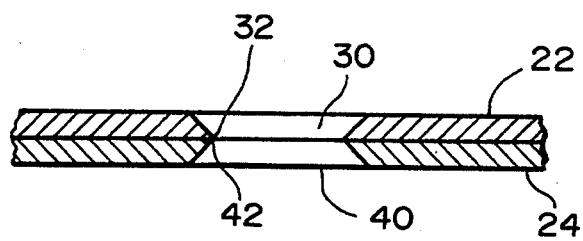
FIG. 5 is a cross-sectional detail of the cutting device of FIG. 4 in its initial, open position.
Figure 6:
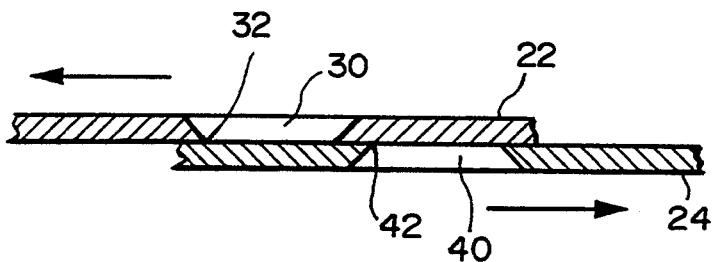
FIG. 6 is a cross-sectional detail of the cutting device of FIG. 4 in its final closed position.

In use, elongated metal bodies 22 and 24 are slidably moved laterally with respect to each other so that openings 30 and 40 are in alignment, as shown in FIG. 5. The cutting device 18 is then placed over the mole 4 and vacuum is applied to the surface of the mole 4, as shown in FIG. 3, to draw mole 4 into elongated tube 8. Force is then exerted on notches 34 and 44 to slidably move elongated metal bodies 22 and 24 inwardly, resulting in severance of mole 4 by cutting edges 32 and 42 (see FIG. 6).

Figure 7:
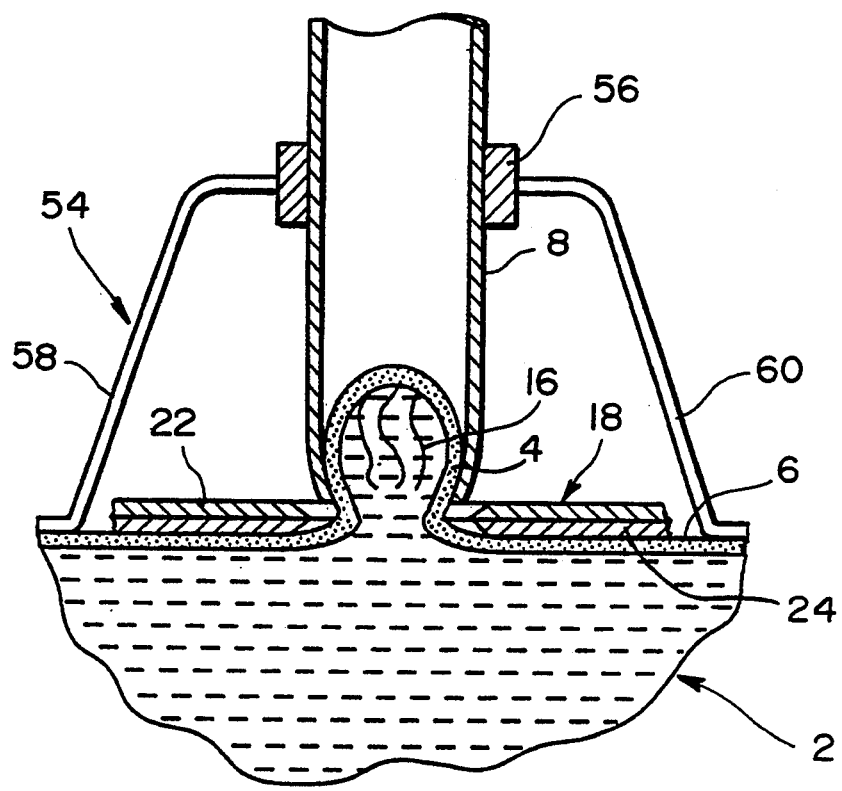
FIG. 7 is a cross-section of the cutting device of FIG. 4 attached to guiding means for the tubular portion of the vacuum means.
Figure 8:
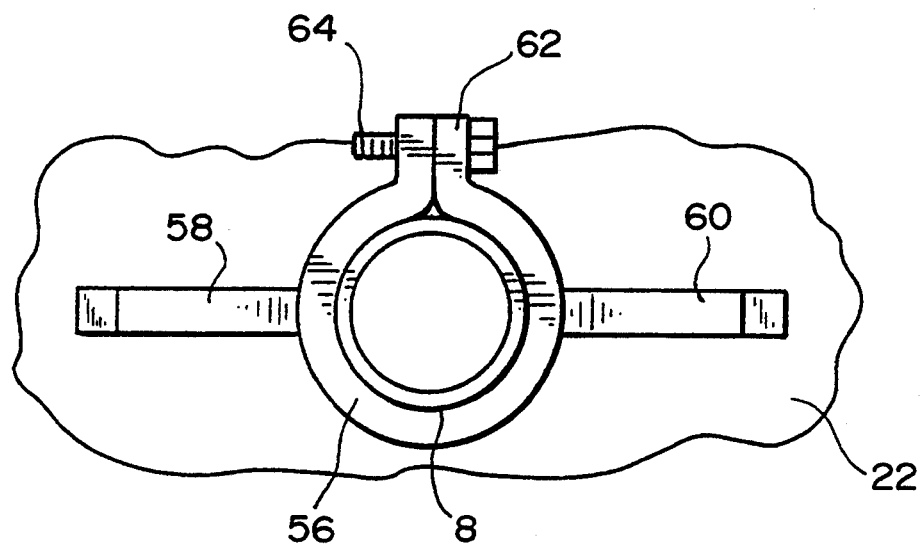
FIG. 8 is a top view, partly in section, showing means to attach the guiding means to the tubular portion of the vacuum means.

As shown in FIG. 7, operation of the surgical device described above can be enhanced by providing the same with a holding or guiding means 54 comprising an annular ring 56, that surrounds elongated tube 8, and supporting legs 58 and 60 that are integral with annular ring 56 and elongated metal body 22. Thus holding or guiding means 54 helps guide elongated tube 8 onto the area to be treated and serves to maintain it in a stable position. Further enhancement is illustrated in FIG. 8 wherein the surgical device is firmly attached to elongated tube 8 by providing annular ring 56 with flanges 62 having aligned threaded openings therein through which a threaded bolt 64 passes.

Figure 9:
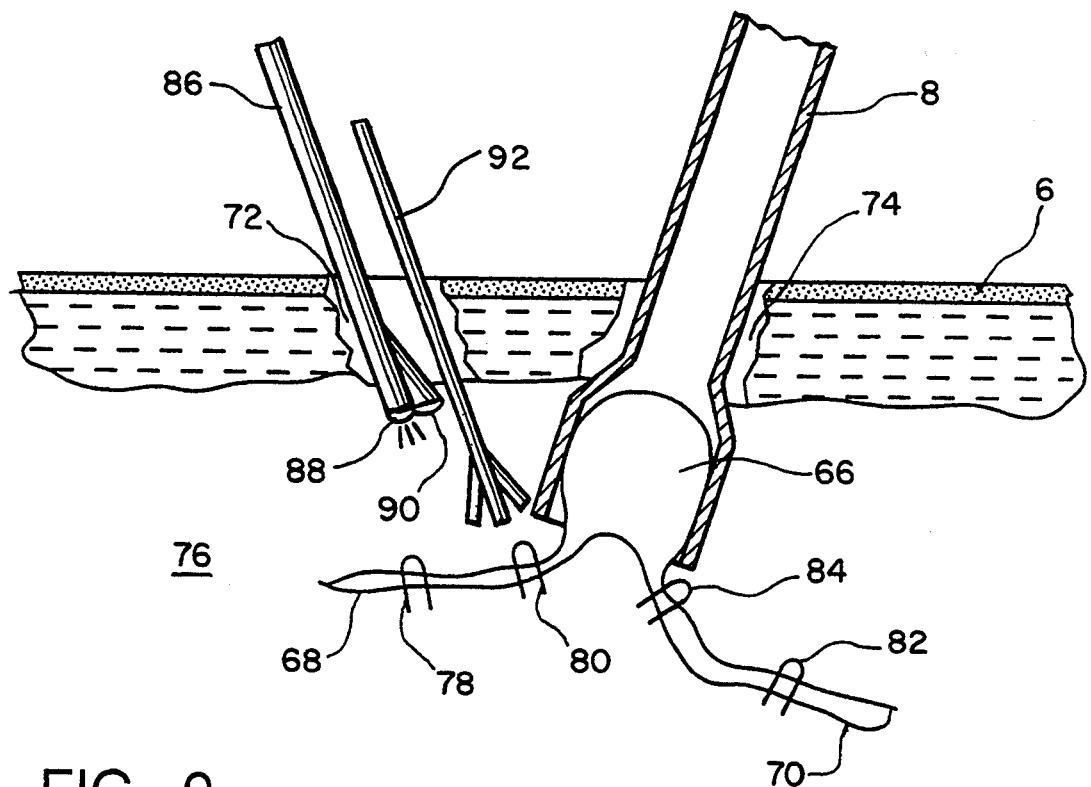
FIG. 9 is a schematic showing the use of the claimed device herein for removal of an organ from the interior of a body.

Although the invention disclosed and claimed herein has been illustrated with the removal of a portion of the body on the external portion thereof, that is, a mole on the skin, it is apparent that it is equally applicable for removal of similar undesirable materials, as well as organs, such as gallbladders, from the interior of the body. Such an embodiment is schematically illustrated in FIG. 9, wherein a gallbladder 66 is to be severed from its associated tubes 68 and 70. Two incisions 72 and 74, each having a length of about two to about four inches, are made to provide access into the body cavity 76. Initially, clamps or sutures 78 and 80 are provided on tube 68 and clamps or sutures 82 and 84 on tube 70 by means of an instrument, not shown, that has been inserted through incision 72, to isolate the gallbladder 66 from tubes 68 and 70 and to facilitate the subsequent cutting operation. Through incision 72 there is then inserted a viewer 86 provided at its lower end with a lamp 88 and a TV camera 90 that communicates with an external TV monitor, not shown. After gallbladder 66 has been moved into elongated tube 8, inserted into body cavity 76 through incision 74, by vacuum means, previously described, cutting means 92, such as previously described, or a laser cutting means or any other suitable cutting means, inserted into the body cavity 76 through incision 72, are guided by an operator, following the course of the operation on the Tv monitor, into position to sever the gallbladder 66 from tubes 68 and 70 by cutting tube 68 between clamps or sutures 78 and 80 and tube 70 between clamps or sutures 82 and 84. The gallbladder 66 can then be drained of bile, by any conventional means, permitting the empty sac to be pulled into elongated tube 8 and then out of body cavity 76. Thus, little damage is done to the protective skin layer, bleeding is minimized and recuperation from such surgery is relatively quickly. The sequence described above can be altered, for example, by inserting the viewer 86 into the body cavity 76 directly after incision, or by taking the gallbladder 66 into said elongated tube 8 before isolating the gallbladder tubes 68 and 70 with clamps or sutures.

Figure 10:
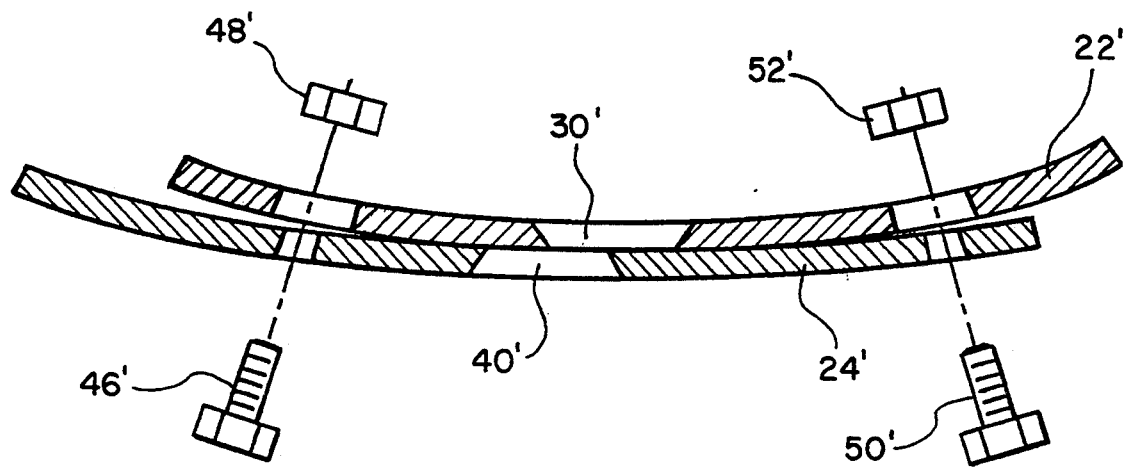
FIG. 10 is a longitudinal cross-section of a cutting device having curved elongated metal bodies.

Although in the above description the cutting device has been shown to be composed of two elongated, essentially flat metal bodies 22 and 24, in a preferred embodiment the metal bodies are curved instead. As shown in FIG. 10, the two metal bodies have different curvatures, so that when the bolts 46' and 50' are tightened, using nuts 48' and 52', respectively, the two metal bodies 22' and 24' will always remain in contact with each other in the cutting zone, thereby assuring effective cutting or shearing action. In addition, in this embodiment wherein the two metal bodies are in curvature, notches 34 and 44, shown in FIG. 4, used to move the two metal bodies 22' and 24', will be elevated and will be more easily accessible to the user.

In a specific example herein, a glass tube having an internal diameter of ¾-inch that was attached to a vacuum source was placed around a pigmented fleshy nevus on the neck of a patient after a local anesthetic was applied to the mole area. A vacuum amounting to 700 mm Hg was then applied to the surface of the mole sufficient to lift the entire mole about ½-inch above the surrounding epidermis, at which point the raised portion was severed from the surrounding epidermis using surgical scissors. There was very little bleeding during the operation and upon healing scarcely any scarring was noted.

Obviously, many modifications and variations of the invention, as hereinabove set forth, can be made without departing from the spit and scope thereof, and therefore only such limitations should be imposed as are indicated in the appended claims.

We claim:

1. Surgical device for removing a portion of a body, which comprises:
    means for applying a vacuum upon the portion of the body sufficient to move the portion of the body to be removed away from the remainder of the body immediately adjacent thereto; and
    cutting means for cutting the portion of the body so moved by said means for applying a vacuum to sever the portion of the body so moved from the remainder of the body, said cutting means including an opening therethrough through which the portion of the body is moved away from the remainder of the body by said means for applying a vacuum,
    said means for applying a vacuum comprising a vacuum source connected to a single elongated tube having a first end and a second end with a cross-section sufficiently large to surround the portion of the body to be removed, one of said ends of said elongated tube being attached to said cutting means so that said elongated tube forms an angle relative to said cutting means with said elongated tube extending over and outwardly from said opening in said cutting means and the body and said other end of said elongated tube being coupled to said vacuum source.

2. The surgical device of claim 1 wherein said cutting means comprises a top and bottom elongated plate, said bottom elongated plate engaging the body and said top elongated plate engaging said bottom elongated plate and being spaced from the body and said elongated plates being slidably mounted to each other and each of said elongated plates being provided with an opening therein capable of being aligned with the other of said openings, each of said openings being provided with cutting edges, said openings in their aligned position being capable of surrounding the portion of the body to be removed and means on said elongated plates to slidably move said elongated plates relative to each other.

3. The surgical device of claim 2 wherein said elongated plates are arcuately curved and extend arcuately away from the body.

4. The surgical device of claim 1 wherein said end of said elongated tube coupled to said cutting means tapers inwardly such that the cross-section of said elongated tube at said end coupled to said cutting means is smaller than the cross-section of the main body of said elongated tube.

5. The surgical device of claim 1, further comprising:
    means for guiding said elongated tube onto the portion of the body to be treated including a first and second guide leg fixedly coupled at one end to said elongated tube.

6. The surgical device of claim 2 wherein said elongated plates are formed of metal.

7. The surgical device of claim 2 wherein said end of said elongated tube attached to said cutting means is attached to said top elongated plate of said cutting means around said opening in said top elongated plate.

8. The surgical device of claim 5 wherein said guiding means includes an annular ring fixedly coupled to said elongated tube and spaced apart from said end of said tube fixedly coupled to said cutting means, said first and second guide bars being fixedly coupled to and extending from said annular ring.

9. A process for surgically removing a portion of a body, which comprises:
    applying a vacuum upon the portion of the body for pulling the portion of the body to be cut away from the remainder of the body immediately adjacent thereto, and
    cutting the portion of the body so moved by moving a cutting device with an opening to sever the portion of the body from the remainder of the body,
    wherein the portion of the body to be cut is removed by applying to the portion of the body to be cut a single elongated tube having a first end and a second end with the first end being attached at an angle to the cutting device over the opening in the cutting device so that the elongated tube extends outwardly, away from the opening in the cutting device and the body and, the first end having a cross-section sufficiently large to surround the portion of the body to be removed, and the second end of the elongated tube being attached to a vacuum source.

10. The process of claim 9 wherein the portion of the body to be removed lies on the body surface.

11. The process of claim 9 wherein the portion of the body to be removed lies in the interior of the body.

12. The process of claim 9 wherein the portion of the body to be removed is a gallbladder

* * * * *